United States Patent [19]

Musson et al.

[11] Patent Number: 5,182,270
[45] Date of Patent: Jan. 26, 1993

[54] STABILIZING PREPARATION FOR THYMOXAMINE

[75] Inventors: Donald G. Musson; Orest Olejnik, both of Upland, Calif.

[73] Assignee: Iolab Corporation, Claremont, Calif.

[21] Appl. No.: 389,153

[22] Filed: Aug. 3, 1989

[51] Int. Cl.$^5$ .................... A61K 31/72; A61K 31/215
[52] U.S. Cl. ...................................... 514/58; 514/546; 536/103
[58] Field of Search .................... 514/58, 546; 536/103

[56] References Cited

PUBLICATIONS

Hirayama et al Chem. Pharm. Bull. 32(10) 4237–4240, 1984.
Riddell et al. Fd. Chem. Toxic 24(7) 469–471, 1986.
Knox et al Fd. Chem. Toxic 24(6) 457–463 1986.
Pagington Chemistry in Britain May, 1987, pp. 455–458.
Szejtli J. of Inclusion Phenomena 135–150, 1983.
Mizutani, et al Iyakuhin Kenkyu 18(5) 1982 pp. 1006–1016.
Prosjocimo, et al American J. of Opthamology vol. 105(3) 1988 pp. 321–322.
Bekers, et al Int. J. Pharm. 1989 52(3) 239–48 Chemical Abstracts, vol. 111, 1989 Abstract 102606e.
Szeitli, J. Inclusion Phenomena 1983 1(2), 1983 135–50 Chemical Abstracts vol. 100, 1984, Abstract 161740a.

Primary Examiner—Robert T. Bond
Assistant Examiner—E. C. Ward
Attorney, Agent, or Firm—Benjamin F. Lambert

[57] ABSTRACT

Experiments have been performed which test the stability of thymoxamine in aqueous solution at room temperature and above. It was determined that dimethyl-beta-cyclodextrin slows the hydrolysis degradation of thymoxamine while other beta-cyclodextrin analogs either accelerate the hydrolysis degradation or have no effect on the rate of hydrolysis degradation. Cytological experiments have been performed which show that chemical formulations containing thymoxamine and up to 5% by weight dimethyl-beta-cyclodextrin have the same toxicity as chemical formulations with thymoxamine alone.

8 Claims, 5 Drawing Sheets

FIG-3 THE FORMATION OF BCD COMPLEXES IN AQUEOUS SOLUTION.

STABILIZING PREPARATION FOR THYMOXAMINE

BACKGROUND OF THE PRIOR ART

1. Field of the Invention

The subject invention is generally directed to the long term storage of thymoxamine at room temperature and, more particularly, to the use of dimethyl-beta-cyclodextrin as a complexing agent to stabilize thymoxamine.

2. Description of the Prior Art

Thymoxamine is a competitive alpha-adrenoceptor blocking agent and has weak anti-histamine activity. The drug has been used in the clinical setting in Europe for causing vasodilation, decreasing blood pressure, and improving blood circulation in the brain. Thymoxamine has been found to reverse mydriasis (prolonged and abnormal dilation of the pupil of an eye) caused by epinephrine or ephredine. Thymoxamine is also commonly known as moxisylyte and has the following chemical formula: 4-[2-(dimethylamino)ethoxy]-2-methyl-5-(1-methylethyl)-phenol acetate. In its clinical applications, thymoxamine typically has a coordinated hydrochloride molecule.

Figure 1:
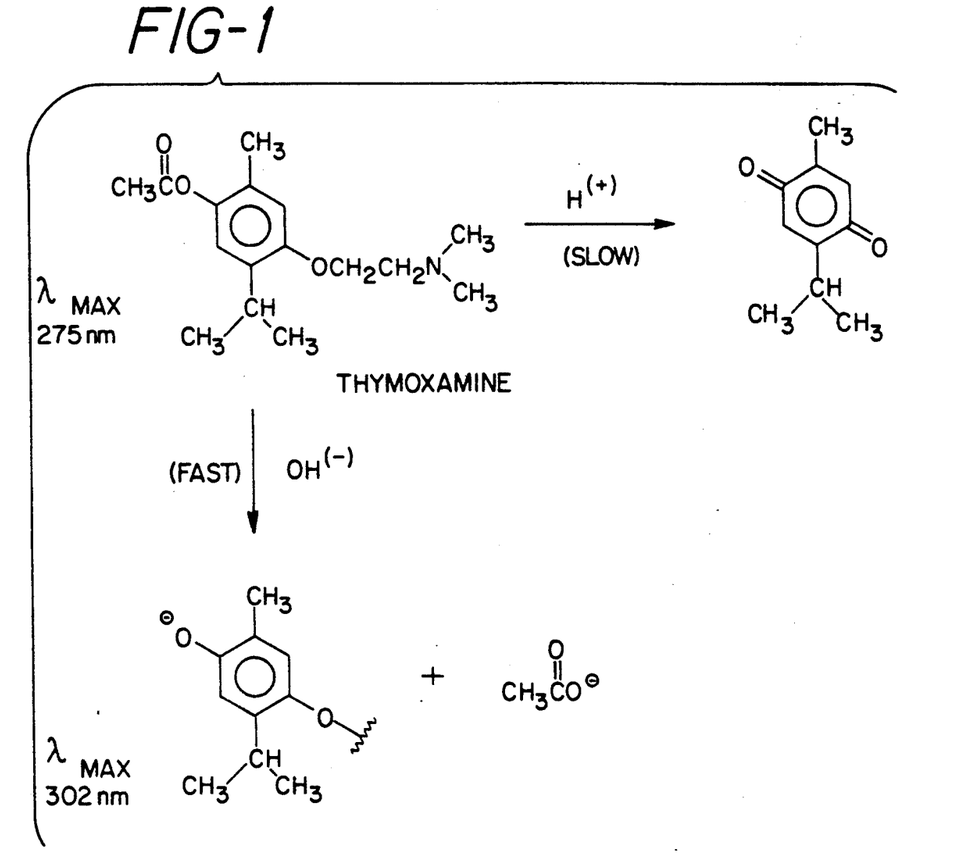
FIG. 1 is a reaction scheme illustrating the hydrolysis of thymoxamine.

FIG. 1 shows that thymoxamine is susceptible to both base and acid catalyzed degradation. The drug contains a phenol acetate moiety which is vulnerable to base catalyzed hydrolysis to a phenol and to acid catalyzed hydrolysis with subsequent oxidation to a quinone. The rate of hydrolysis of thymoxamine is pseudo-first-order and takes many days at pH levels between 2 and 7; however, at high pH levels, the rate of hydrolysis is on the order of minutes. The hydrolysis of thymoxamine gives a linear Arrhenius plot in water from 40° to 60° C.

Long term storage of the drug at room temperature has not been possible because of the hydrolysis problems. Giovanni, in *J. of Ophthalmology*, 105(3), 1988, page 32, has reported that solutions of thymoxamine are not stable at ambient temperature unless refrigerated. The formulation specifications for refrigerated thymoxamine require a pH range of 4.4 to 6.4; however, control of the pH in the formulation has not provided completely satisfactory results.

Figure 2:
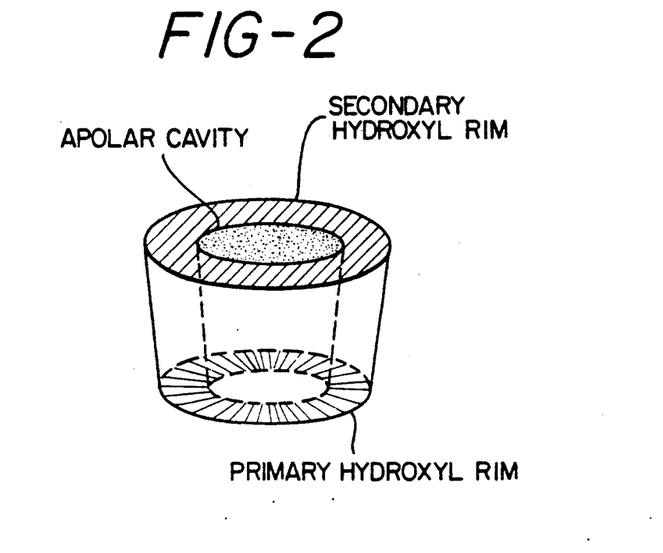
FIG. 2 is a three dimensional sketch of the torroidal shape of beta-cyclodextrin.

FIG. 2 shows the torroidal shape of a beta-cyclodextrin molecule. The primary hydroxyl groups project from one outer edge and the secondary hydroxyl groups project from the other. The result is a molecule with a hydrophobic center and a relatively hydrophilic outer surface. Beta-cyclodextrin's have been used to enhance the solubility and stability of drugs in aqueous solution. Passington, in *Chemistry of Britain*, May 1987, page 457, has reported that beta-cyclodextrin complexes or "inclusion compounds" enhance the solubility of prostoglandins, steroid hormones, diuretics, and barbiturates, stabilize the hydrolysis of aspirin, atropine, and procaine, stabilize the oxidation of chlorpromazine and epinephrine, stabilize the dehydration of prostaglandin E groups, and enhance the bio-availability of aspirin, phenytoin, and digoxin. In addition, beta-cyclodextrins prevent evaporation, improve the bad smell of various drugs, reduce stomach injury, and inhibit hemolysis. Studies have shown that benzocaine complexed with beta-cyclodextrin does not undergo alkaline hydrolysis while dissociated benzocaine does.

Figure 3:
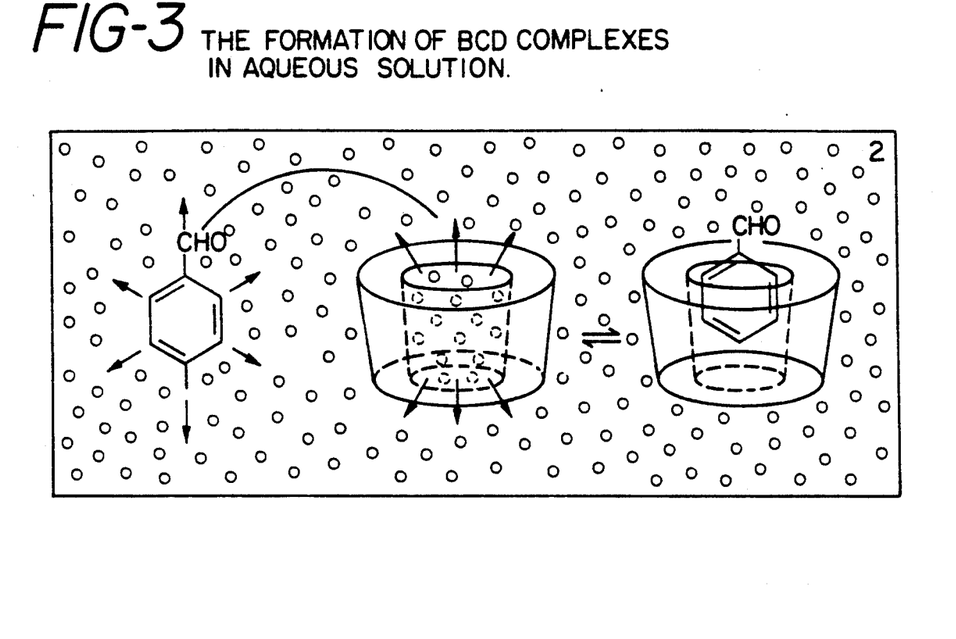
FIG. 3 is a reaction scheme illustrating the formation of an inclusion complex With a cyclodextrin molecule.

FIG. 3 shows complexation with betacyclodextrin is a reversible process. In aqueous solution, the guest molecule penetrates into the hydrophobic cavity forming a complex or "inclusion compound", and the exterior of the betacyclodextrin becomes hydrated. Dissociation of the beta-cyclodextrin complex is governed by the guest material. The stability of many beta-cyclodextrin complexes in aqueous solution can speed up or slow down a chemical reaction. For example, studies of aminobenzoic acids have revealed that when the reactive groups are within the beta-cyclodextrin cavity, the rate of hydrolysis decreases; however, if the active groups are outside the cavity the hydrolysis rate increases.

Figure 4:
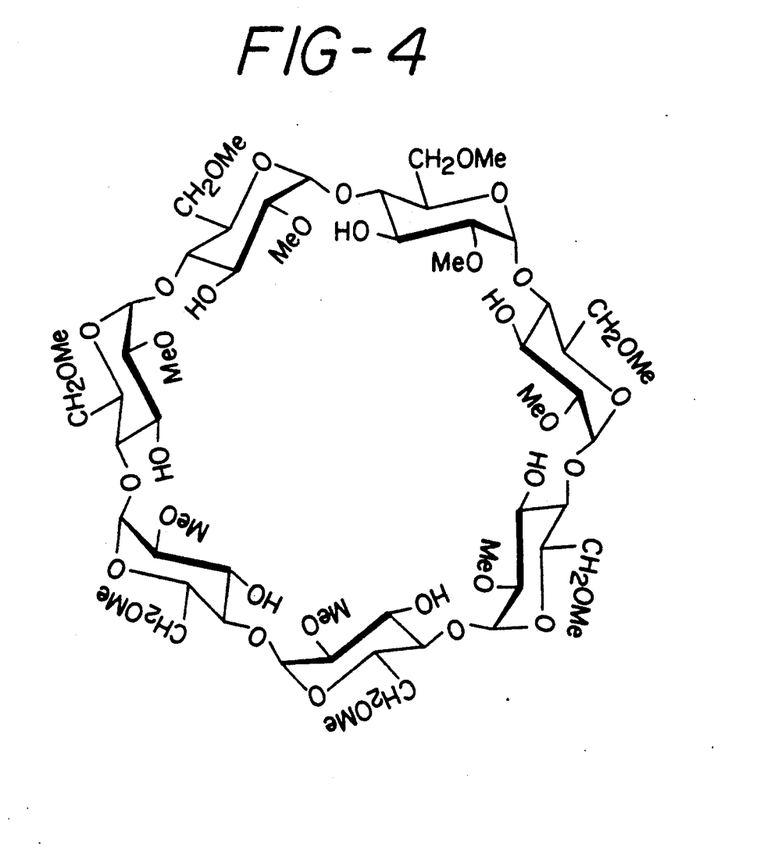
FIG. 4 is a drawing of the chemical structure of DMBCD.

FIG. 4 shows heptakis-2,6-di-O-methyl-beta-cyclodextrin which is often abbreviated a dimethyl-beta-cyclodextrin (DMBCD). DMBCD is prepared by selective methylation of the C(2) and C(6) primary hydroxyls of beta-cyclodextrin while the C(3) hydroxyls remain unsubstituted. DMBCD has a torroidal shape similar to that shown in FIG. 2 and inclusion complexes are formed with DMBCD in a manner similar to that shown in FIG. 3.

Szejtli, in *Journal of Inclusion Phenomena*, 1, 1983, pages 135-150, examined the use of DMBCD as a parenteral drug carrier. DMBCD does not cause the renal toxicity that beta-cyclodextrin causes and is more soluble than beta-cyclodextrin. DMBCD was found to enhance the solubility of lidocaine, marcaine, vitamin $D_3$ and vitamin $K_3$ by forming an inclusion complex with those molecules. The diffusion rate of a parenterally administered drug complexed with DMBCD was slowed such that the time duration for which an anesthesia remained effective was extended. In addition, complexing vitamins with DMBCD decreased the level of free vitamin and thereby reduced vitamin toxicity.

No studies have discussed the possibility of complexing DMBCD with thymoxamine for the purpose of preventing hydrolysis. Before the invention thereof by the applicants, it was not known that thymoxamine could form an inclusion compound with DMBCD. Moreover, before the invention thereof by the applicants, it was not known that thymoxamine would be stabilized by formation of an inclusion complex, i.e., as noted above, inclusion complexes can sometimes speed up a chemical reaction rather than slow it down.

SUMMARY OF THE INVENTION

It is therefore an object of this invention to provide a formulation of thymoxamine which is suitable for long term storage at room temperature.

It is another object of this invention to provide a formulation of thymoxamine which includes DMBCD used as a stabilizing agent to prevent hydrolysis of thymoxamine.

According to the invention, experiments have been performed which show that DMBCD can stabilize thymoxamine from hydrolysis.

A long term stability study performed on thymoxamine formulations currently available showed a decrease to less than 80% of the initial concentration of the thymoxamine when stored at room temperature. The study clearly shows that altering the pH of the thymoxamine formulation will not prevent hydrolysis of thymoxamine at room temperature. In order to study the stabilizing effects of DMBCD as well as other beta-cyclodextrins on thymoxamine, a quick, non-specific assay using an ultraviolet (UV) spectrophotometer and a slower, specific assay using HPLC-UV were developed to monitor the formation of the phenolate anion. An accelerated stability study performed on a thymoxamine formulation using the UV, and HPLC-UV assays described above showed that the hydrolysis of thymoxamine, initiated with a 1% solution of NaOH, and formation of its phenolate anion degradate can be monitored from beginning to end within thirty to fifty minutes.

The accelerated assay techniques for monitoring the degradation of thymoxamine were used to analyze the stabilizing effects of beta-cyclodextrin analogs on thymoxamine in aqueous solutions. In general, kinetic studies show that beta-cyclodextrin, hydroxypropyl-beta-cyclodextrin and similar analogs accelerate the hydrolysis of thymoxamine under alkaline conditions when compared to thymoxamine alone. DMBCD slows the hydrolysis of thymoxamine under alkaline conditions, and trimethyl-beta-cyclodextrin seems to have little effect. In addition, it was determined that increases in the molar ratio of DMBCD to thymoxamine causes decreases in the rate constant.

Results from the accelerated stability studies were used in formulating a solution of thymoxamine complexed with DMBCD. A long term shelf life study was performed at room temperature and 45° C. on the thymoxamine/DMBCD formulation which revealed that the formulation was stable under these adverse storage conditions.

In addition, cytotoxicity experiments were performed to determine the cytotoxicity of the thymoxamine/DMBCD formulation. The toxicity of a thymoxamine formulation without DMBCD was comparable to formulations containing 1, 2.5, and 5% concentrations of DMBCD.

BRIEF DESCRIPTION OF THE DRAWINGS

The foregoing and other objects, aspects and advantages of the invention will be better understood from the following detailed description of a preferred embodiment of the invention with reference to the accompanying drawings in which.

DETAILED DESCRIPTION OF THE PREFERRED EMBODIMENTS OF THE INVENTION

Referring now to the drawings and, more particularly to FIG. 1, there is shown a reaction scheme for the hydrolysis of thymoxamine in acid and base environments. Mizutani et al., in *Iyakuhin Kenkyu*, 13(5), (1982), pages 1006–1016, reported the degradation of thymoxamine is pseudofirst order and gives a linear Arrhenious plot in water from 40° to 60° C. In that same article, the log K-pH profile gives a nadir (depression) at pH 5. The formulation specifications for refrigerated thymoxamine call for a pH range of 4.4 to 6.4.

A long term stability study was set-up with three thymoxamine formulations prepared at pH 6.49, pH 5.07, and pH 4.21 respectively. The formulations contained 1.0 mg/ml thymoxamine, 0.3 mg/ml disodium edetate (EDTA), 0.1 mg/ml benzalkonium chloride, 0.1 mg/ml Na-Phosphate monobasic, 2.5 mg/ml Na-Phosphate dibasic, and 7.0 mg/ml sodium chloride, diluted with water to 100 ml. Thymoxamine was obtained from the Geodecke company of Freiburg, West Germany. The benzalkonium chloride solution was obtained as a 50% solution from Onyx Chemical Company of Jersey City, N.J. The disodium EDTA was obtained from the Ciba-Geigy company of Summit, N.J. The water was deionized and was continuously distilled. The pH of the three formulations was adjusted with dilute HCl to 6.49, 5.07, and 4.21, respectively, and the tonicity of the formulations was adjusted with sodium chloride to approximately 300 mOsm. Table 1 shows the long term degradation of the thymoxamine in terms of the percentage of thymoxamine measured in the formulation relative the total amount thymoxamine in the formulation at the beginning of the study in the three formulations at room temperature and at 45° C. over a three month period.

TABLE 1

| Week | pH (RT) | | | pH (45°) | | |
|---|---|---|---|---|---|---|
| | 6.49 | 5.07 | 4.21 | 6.49 | 5.07 | 4.21 |
| 1 | 0.903 | 0.960 | 0.949 | 0.759 | 0.942 | 0.933 |
| 12 | 0.770 | 0.780 | — | 0.233 | 0.777 | 0.737 |

The analytical procedure to quantify thymoxamine over long term storage at room temperature and at 45° involved similar methodology to the HPLC-UV specific assay described infra. The percentage of the original thymoxamine was determined using a Waters ® 6000 HPLC pump, a Waters ® WISP 710 autosampler, a Kratos ® 773 UV detector set at 280 nm, a Chemcosorb ®-5-ODS-H column (150 * 4.6 mm), and a computing integrator involving a Nelson Analytical Data System ®. In the mobile phase, 13.8 g. of sodium phosphate monobasic was mixed with 700 ml. of water. Then, 4 ml. of glacial acetic acid and 10 mg. of tetrabutyl ammonium hydrogensulfate was added to the above and the solution was diluted to one liter. The mobile phase was then filtered through a 0.3 micron glass filter. The flow rate through the system was 1.0 ml/min. The injection volume of the thymoxamine formulation under test was 20 μl and the retention time was 7.2 min.

The data in Table 1 show a loss of thymoxamine to less than 80% of the initial concentration for the three formulations at both temperatures. The pH for all the formulations changed towards the acidic range. It can be concluded from Table 1 that controlling the pH alone will not stabilize thymoxamine for room temperature storage.

FIG. 1 shows thymoxamine has a phenol acetate moiety which absorbs at 275 nm. In the presence of base catalysis, the ester will hydrolyze to the phenolate anion which absorbs at 302 nm. A non-specific assay using an ultra-violet (UV) spectrophotometer available from the Perkin Elmer company of Connecticut, has been developed to monitor this chromophoric change.

Figure 5A:
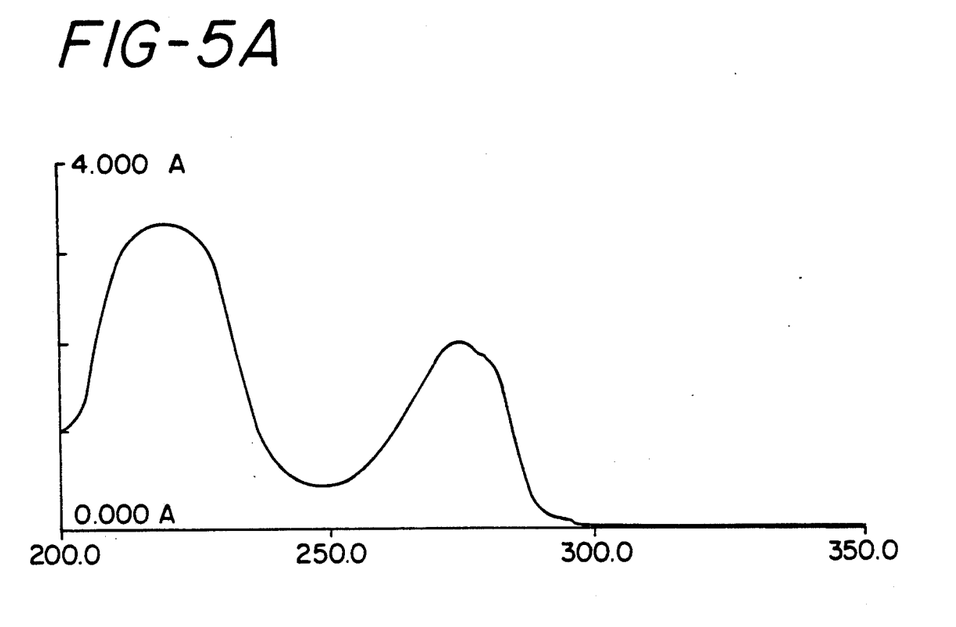
FIGS. 5A and 5B show ultraviolet absorbance spectrums for thymoxamine alone and thymoxamine with base added, respectively.
Figure 5B:
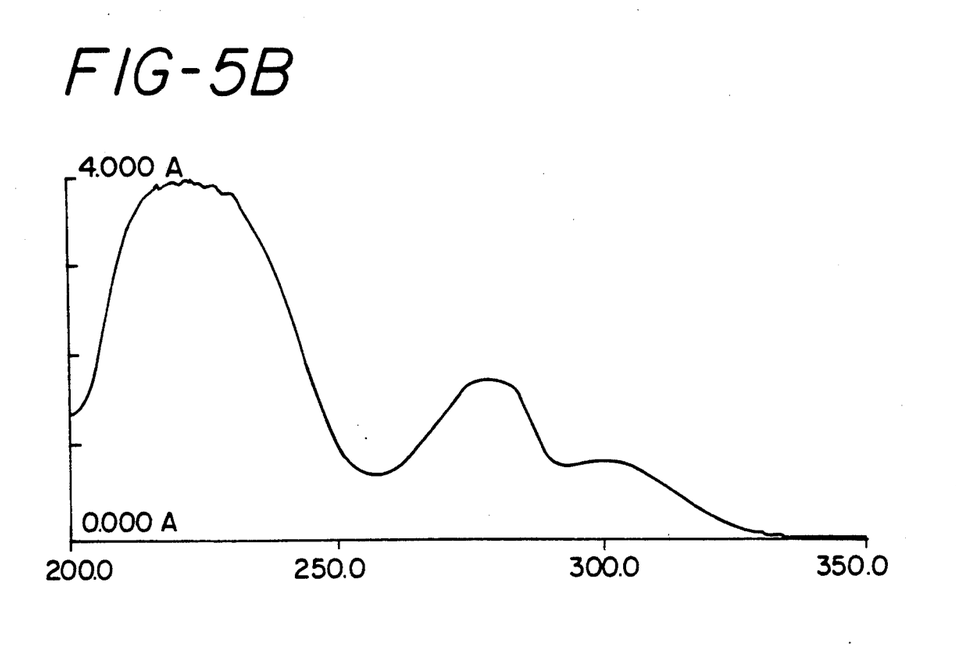

FIGS. 5A and 5B shows a bathochromic shift between a solution containing thymoxamine alone and a solution containing thymoxamine with base added (approximately 5 mM NaOH), respectively. The spectra were obtained with a Perkin Elmer, Lambda 4B UV/Vis spectrophotometer scanning from 200 to 350 nm at a scanning speed of 200 nm/min and slit width set at 1 mm. Chromophoric changes are measured in absorbance units only and a standard calibration curve was not used. 10 mm rectangular sample and reference cells, available from Fisher Scientific, were used for the experiment. Several scans are made over time until enough data points are recorded for generating the spectrum. The reference and sample cells each contained water and NaOH. The sample cell in FIG. 5A contained 1.34 mg of thymoxamine (free base) available from stock solution of 1.34 mg/ml. The sample cell in FIG. 5B was identical to that of 5A except that 60 µl of 1% NaOH was added one minute prior to measurement in the spectrophotometer. The run time for the UV assay is less than three minutes.

Occasionally, the UV spectrophotometer will produce a spectrum without a clear distinction between the UV bands of thymoxamine and the phenolate anion degradation. In those situations, a specific assay using reverse-phase, high performance liquid chromatography (HPLC) and a diode array at 200-350 nm or a UV/Vis absorbance detector at 275 nm can be used to separate the thymoxamine from the phenolate anion degradation. The HPLC system used in the experiments comprised a Waters ® 600E PowerLine module (high performance delivery with PowerLine HPLC system control), a Waters ® 990 photodiode array which emits wavelengths of light in the 200 to 350 nm region (an Applied BioSystems 783a Programmable Absorbance Detector at 275 nm can be substituted therefor), and a Waters ® 712 Waters Intelligent Sample Processor (WISP). The column used was a UBondpak C18 having 10 µm particle size. The mobile phase contained 30% 2-propanol/70% Na-Phosphate buffer (4 ml of phosphoric acid in two liters of water, pH adjusted with 1M NaOH to 6.0). The mobile phase was filtered through a 0.45 micron nylon filter under vacuum. The flow rate for the HPLC system was 1.0 ml/min and the sample injection volume was 10 µl.

Figure 6A:
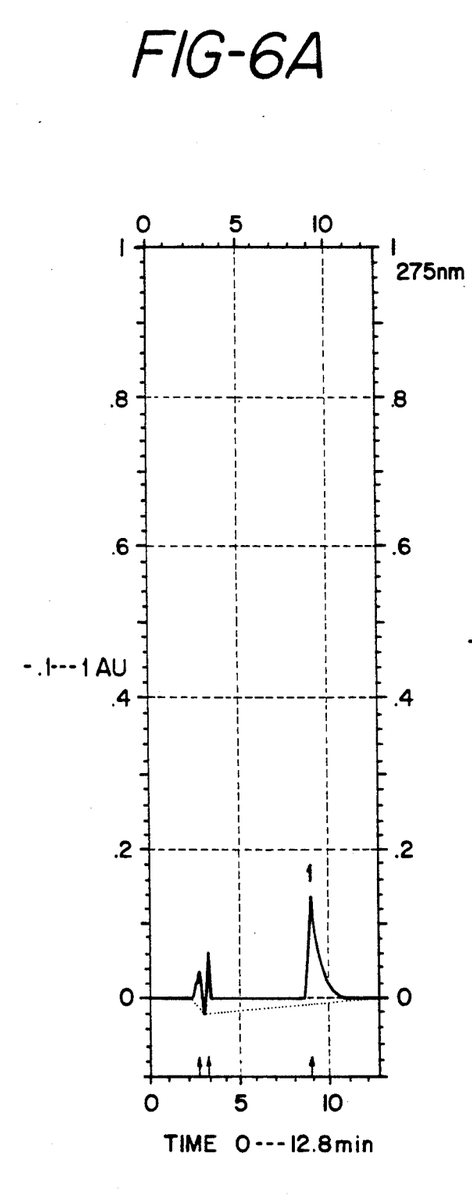
FIGS. 6A and 6B show HPLC-UV chromatograms for thymoxamine alone and thymoxamine with base added, respectively.
Figure 6B:
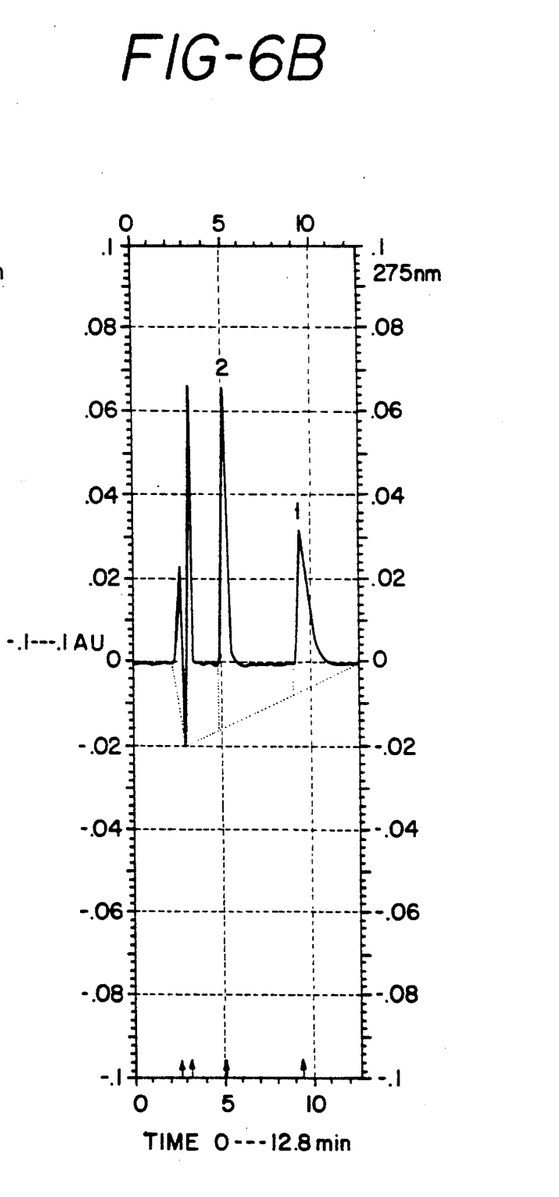

FIGS. 6A and 6B show chromatograms of a sample containing thymoxamine only and a sample containing thymoxamine after the addition of base (5 mM NaOH), respectively. Thymoxamine is indicated by peak (1) and the phenol degradate is indicated by peak (2). The degradate (2) elutes before thymoxamine (1) and is separated by about four minutes In the experiments, a 10 µl aliquot of sample is removed from the reaction and injected into the HPLC column without any prior preparation. The run-time for the HPLC-UV assay is about ten minutes.

Figure 7:
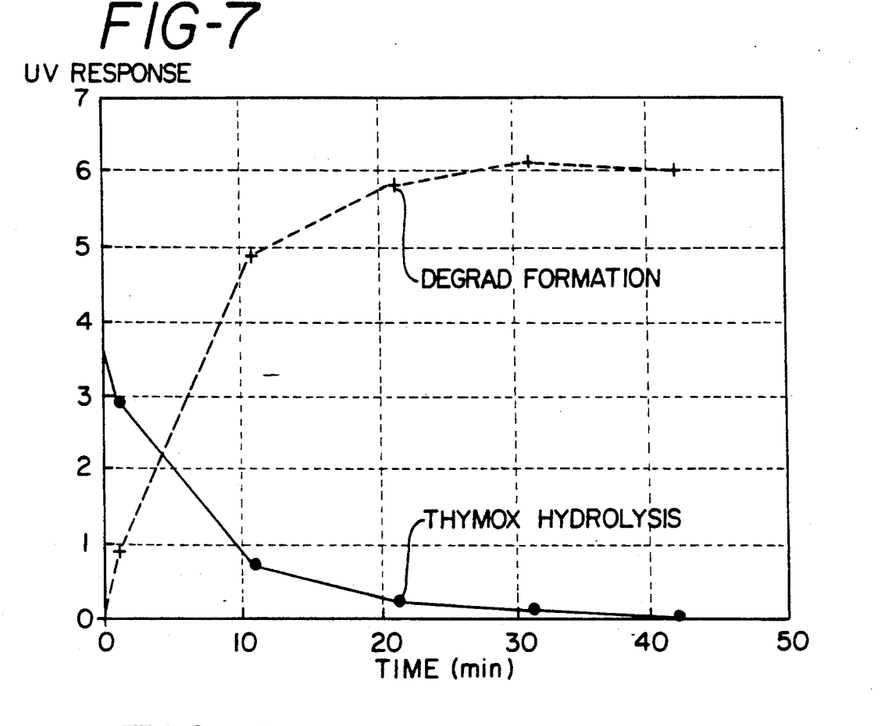
FIG. 7 is a graph showing the loss of thymoxamine and the formation of its degradate over time.

FIG. 7 shows that the loss of thymoxamine and the formation of its phenolate anion degradate can be monitored from beginning to end in thirty to fifty minutes using the UV-non-specific and HPLC-UV-specific assays described above. The y-axis shows the UV response in terms of absorbance units. Twenty microliters of NaOH was added to the sample cell to start the hydrolysis reaction. The kinetic half life ($t_{\frac{1}{2}}$) of degradation was determined to be 5.11 minutes when using the HPLC-UV assay and 4.92 minutes when using the UV assay.

The discussion related to FIGS. 5A, 5B, 6A, 6B, and 7 clearly demonstrates that the accelerated stability test, involving UV-non-specific and HPLC-UV-specific assays, can be used to monitor the hydrolysis reaction of thymoxamine in aqueous solution. Hirayama et al., in *Chem. Pharm. Bull.* 321(10), (1984), page 4237, has reported that analogs of beta-cyclodextrin stabilize solutions of a variety of compounds (e.g., prostaglandin E2 and A2 using methylated beta-cyclodextrins). The applicants have used the stability indicating assays described above to investigate the stabilizing effects of beta-cyclodextrin analogs on thymoxamine in aqueous solution. The beta-cyclodextrin analogs were obtained from Janssen and Janssen of Beerse, Belgium. DMBCD was also obtained from American Tokyo Kasel company of Portland, Oreg.

In the base catalyzed hydrolysis of thymoxamine (accelerated stability test), the UV analysis and HPLC-UV analysis were performed according to the following techniques. Under UV analysis, the degradation of a 2 ml sample containing thymoxamine was initiated by the addition of 60 µl of 1% NaOH (a 1 ml sample was initiated by the addition of 30 µl). The base was also added to the reference cell (which does not contain thymoxamine). Preparation of a sample involved mixing an aliquot (0.5 to 1 ml) of thymoxamine HCl from the stock solution with an equal volume of a beta-cyclodextrin analog solution. The sample may be diluted further with deionized water depending on the experiment. The spectrophotometer was scanned repeatedly until enough data had been obtained. Under HPLC-UV analysis, the degradation of a 1 ml sample involved the addition of 30 µl of 1% NaOH. Preparation of the sample included the addition of 10 µl of thymoxamine stock solution to 1 ml of a 10% solution of a beta-cyclodextrin. The sample was repeatedly chromatographed until enough data had been obtained.

Table 2 shows the stability of thymoxamine in the presence of dimethyl-beta-cyclodextrin (DMBCD), hydroxypropyl-beta-cyclodextrin (HPBCD), and trimethyl-beta-cyclodextrin (TMBCD).

TABLE 2

| Cyclodextrin in sample | $T_{\frac{1}{2}}$ (min) | Rate K (min$^{-1}$) | Relative Rates |
|---|---|---|---|
| none | 4.10 | 0.169 | 1 |
| DMBCD | 44.1 | 0.0157 | 0.093 |
| HPBCD | <1 | >0.693 | >4.10 |
| TMBCD | 4.61 | 0.150 | 0.898 |

In the experiment, the thymoxamine concentration was 0.01 g/ml and beta-cyclodextrin concentrations were 10% w/w. The 10% concentration of DMBCD significantly stabilized thymoxamine compared to HPBCD or TMBCD. Both HPBCD and TMBCD accelerated the hydrolysis of thymoxamine when compared to a neat solution. The results of the applicants affirm in part the result of Hiryama et al., ibid., who found that DMBCD had superior stabilizing properties compared to TMBCD. The kinetic differences between HPBCD and DMBCD may be due to localized hydroxyl groups in the hydroxypropyl complex catalyzing the ester hydrolysis. The differences between DMBCD and TMBCD may be a result of conformational differences in the hydrophobic cavity, i.e., there may be greater stearic hindrance to the penetration of TMBCD with the thymoxamine guest molecule since its cyclic ring is distorted from the regular heptagonal symmetry of DMBCD.

A variety of other beta-cyclodextrin analogs, including beta-cyclodextrin (BCD), methyliertis BCD, methyl-HPBCD, methyl-hydroxyethyl-beta-cyclodextrin (methyl-HEBCD), and poly-beta-cyclodextrin (poly-BCD), were tested under the accelerated stability test conditions outlined above (thymoxamine HCl concentration equal to 0.01 g/ml aqueous solution, concentrations of the beta-cyclodextrin analog prepared at 10% w/w (except the beta-cyclodextrin (BCD) molecule alone was prepared in a saturated solution at 5% w/w)). Each of these beta-cyclodextrin analogs, including BCD and polyBCD, accelerated the rate of hydrolysis of thymoxamine relative to a neat solution. The $t_{\frac{1}{2}}$ was less than one for all of these analogs, indicating the reaction was faster than could be measured by HPLC. Chromophoric changes observed on the UV spectrophotometer with HPBCD and methyl-HPBCD were instantaneous from one run to the next.

Table 3 shows that a concentration dependent relationship exists between the molar ratio of DMBCD to thymoxamine (DMBCD/Thymox) and the rate of hydrolysis of thymoxamine.

TABLE 3

| Molar Ratio | $T_{\frac{1}{2}}$ (min) | Rate K (min$^{-1}$) | Relative Rate |
|---|---|---|---|
| Thymoxamine | 1.85 | 0.375 | 1 |
| 1.3:1 | 4.6 | 0.151 | 0.403 |
| 3.4:1 | 6.48 | 0.107 | 0.285 |
| 6.7:1 | 12.22 | 0.0567 | 0.1512 |
| 13:4 | 20.19 | 0.0343 | 0.0915 |

The thymoxamine HCl concentration was 0.275 g/ml and the molar ratio was based on DMBCD having a molecular weight of 1330. It is important to note that 1330 is the theoretical number computed by adding the two methyl groups on each sugar unit of the beta-cyclodextrin and that the synthesis of DMBCD does not ordinarily give a pure compound with a with a molecular weight of 1330. DMBCD usually has a molecular weight range or degree of substitution determined by the procedure of synthesis and purification. The molecular weight range may be different from supplier to supplier. Szejtli, in *J. of Inclusion Phenomena*, 1:135–150, 1983, has outlined some general physical characteristics of DMBCD.

Table 3 shows that as the ratio of DMBCD to thymoxamine increases, the rate constant decreases. This result corresponds to that of Hirayama et al., ibid., who found that the stabilizing effects of methylated beta-cyclodextrins increase with concentration or molar ratio of the beta-cyclodextrin to the unstable drug. The rate of hydrolysis appears dependent on the molar ratio of DMBCD to thymoxamine, but not on the concentration of the complex at a fixed ratio. Therefore, increasing the amount of DMBCD relative to thymoxamine in an ophthalmic solution will provide more stabilization, but, changing the concentration of the thymoxamine/DMBCD inclusion compound in solution will not affect the stabilization. The toxicity of DMBCD sets an upper limit for the amount DMBCD which can be included in a formulation.

The effectiveness of DMBCD in stabilizing thymoxamine in a formulation containing polyvinyl alcohol, dextrose, disodium EDTA and benzalkonium chloride was tested using the accelerated stability conditions. Note that the previous preparations discussed in conjunction with Table 1 contained a strong buffer, sodium phosphate, to prevent pH drift with time so that the importance of pH on the degradation of thymoxamine could be determined. However, the presence of sodium phosphate buffer at pH 5.0 in an ophthalmic formulation would be irritating to the eyes; therefore, an ophthalmic preparation without a buffer is preferred. In the present preparation, dextrose is used to adjust osmolality and polyvinyl alcohol is used to adjust viscosity.

The formulations used in the accelerated stability test were comprised of the following: 1.1 mg/ml thymoxamine HCl, 10.0 mg/ml polyvinyl alcohol, 38.0 mg/ml dextrose, 0.3 mg/ml disodium edetate, and 0.1 mg/ml benzalkonium chloride. The stabilized formulation contained 25.0 mg/ml DMBCD, while the unstabilized formulation did not contain any DMBCD. The formulations were diluted to 200 ml with continuously distilled water. The relative rate of hydrolysis of the DMBCD stabilized formulation compared to the unstabilized formulation was 0.1134. The results clearly indicate the chemical hydrolysis of thymoxamine can be slowed by formation of a inclusion complex with DMBCD.

The proper concentration range of thymoxamine in a formulation depends on its possible therapeutic uses, i.e., a 0.1% solution is suitable for the reversal of pheneylphrine induced mydriasis and a 0.5% solution is suitable for the treatment of pigmentary glaucoma. It is anticipated that the concentration of thymoxamine HCl in an ophthalmic solution can range from 0.05% to 1.0%. The concentration range of DMBCD is determined by its toxicity (upper limit) and its stabilizing effects (lower limit). In Table 3, it is shown that a formulation having a molar ratio of 1.3:1 for DMBCD relative to thymoxamine has a stabilization effect of greater than twice that for thymoxamine in solution alone. Thus, a slight molar excess of DMBCD relative to thymoxamine should provide the long-term shelf life needed at room temperature. A concentration range of 0.5 to 5.0% DMBCD should be suitable for an ophthalmic solution. The concentration ranges for the excipients should allow for variance and modification as needed in order to adjust viscosity, osmolality, and preservative effectiveness. Table 4 outlines the ranges of suitable ophthalmic formulations which stabilize thymoxamine at room temperature.

TABLE 4

| Chemical Component | Concentration Range (weight %) | mg/ml diluted to 200 ml. |
|---|---|---|
| Thymoxamine HCl | 0.05 to 1.0 | 0.5 to 10 |
| Polyvinyl alcohol | 0.05 to 2.5 | 0.5 to 25 |
| Dextrose | 2.0 to 8.0 | 20 to 80 |
| Disodium edetate | 0.01 to 0.06 | 0.1 to 0.6 |
| Benzalkonium chloride | 0.004 to .04 | 0.04 to 0.2 |
| DMBCD | 0.5 to 5.0 | 5 to 50 |

In the formulation, dextrose may be replaced by sodium chloride at a weight percent range of 0.0 to 1.0% (0 to 10 mg/ml in a solution which is made by diluting with water to 200 ml).

Based on the results of the accelerated stability studies on the beta-cyclodextrin analogs discussed above, a long term shelf life study of thymoxamine formulations was performed. The long term shelf life study was similar to that discussed in reference to table 1. Two formulations were prepared: one with DMBCD and one without DMBCD. The formulations contained (25 mg/ml DMBCD), 1 mg/ml thymoxamine HCL, 10 mg/ml polyvinyl alcohol, 41 mg/ml dextrose, 0.3 mg/ml disodium EDTA, and 0.1 mg/ml benzalkonium chloride. In the formulation with DMBCD, the molar ratio of DMBCD to thymoxamine is 5.9297. The formulations were filtered through 0.2 μm Tuffryn, available from Gelman Sciences of Ann Arbor, Mich. The tonicities of the formulations were adjusted with dextrose to 300 mOsm/kg. The final pH of the formulations was adjusted to 5.0 with HCl. The two formulations were divided into two groups where one of each group was stored at room temperature and the other was stored at 45° C. The formulations were analyzed for thymoxamine over time.

Figure 8:
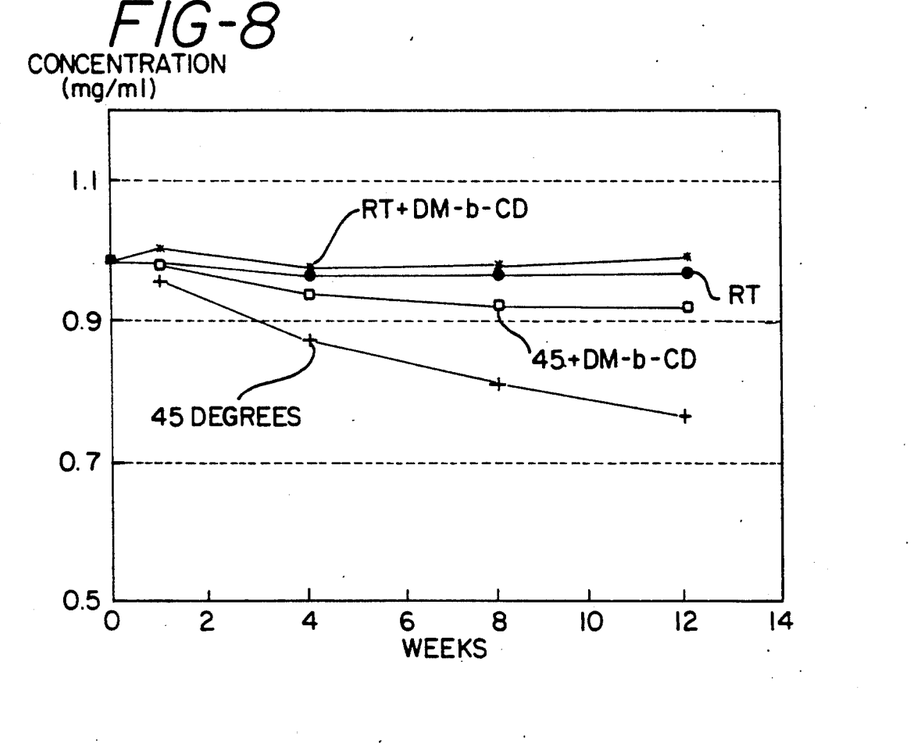
FIG. 8 is a graph showing the concentration of thymoxamine over a three month period under room temperature and 45° C. storage conditions.

FIG. 8 shows the long term degradation of thymoxamine in its formulation with and without DMBCD. Only the sample without DMBCD stored at 45° C. fell below 90% of its initial concentration within one month (i.e., the initial concentration of thymoxamine HCl was 1 mg/ml and FIG. 8 shows the sample without DMBCD stored at 45° C. below 0.9 mg/ml after four weeks). The pH of most of the formulations changed towards the acidic range of 4.57 to 5.06. The apparent contradiction between the results shown in FIG. 8 for a thymoxamine formulation without DMBCD and the results shown in Table 1 for a thymoxamine formulation without DMBCD may be the result of the presence or absence of certain excipients, such as phosphate buffer, dextrose, polyvinyl alcohol and/or sodium chloride.

Four formulations of thymoxamine with and without DMBCD were tested for cytotoxicity to 3T3-L1 mouse embryo cells. The cells (#CL92.0) are available from the American Type Culture Collection of Rockville, Md. The four formulations comprised a control, a 1% DMBCD w/w, a 2.5% DMBCD w/w, and a 5.0% DMBCD, and each formulation included 1.0 mg/ml thymoxamine HCl, 10.0 mg/ml polyvinyl alcohol, 41.0 mg/ml dextrose, 0.3 mg/ml disodium EDTA, and 0.1 mg/ml benzalkonium chloride. The formulations were diluted with purified water to a total volume of 200 ml. The pH of each formulation was adjusted to 5.12±0.05 with HCl. The tonicity of each formulation was adjusted to 301±10 mOsm. The formulations were sterilized by ultrafiltration using 0.2 μm Tuffryn.

The cytotoxicity of each formulation to the 3T3-L1 cells was determined according to the Frame Kenacid blue method discussed in Riddell et al, *Fd Chem. Toxic.*, 24 (1986), pages 461-469, and Knox et al., *Fd. Chem. Toxic.*, 24 (1986) pages 463-467. This test involves the measurement of total cellular protein by a dye-binding method after an appropriate period of continuous exposure to the test chemical. A dose response curve was constructed to determine the ID$_{50}$ of each formulation that reduced the final total cellular protein by 50% in comparison with that of the control cell walls. The dose response curve is constructed according to Greaves et al., report from Queen's Medical Center, Nottingham, England NG7 2UH, and that reference is herein incorporated by reference.

Table 5 shows the comparable toxicity of a thymoxamine formulation without DMBCD and formulations with 1, 2.5, and 5% concentrations of DMBCD.

TABLE 5

| [DMBCD] mg/ml | ID-50 mg/ml | ID-80 mg/ml | % 3T3-L1 cell survival exposure time | | |
|---|---|---|---|---|---|
| | | | 1 min | 5 min | 10 min |
| control (0) | 27.95 ±2.78* | 52.28 ±1.07 | 90.5 ±1.7* | 74.0 ±6.1 | 66.0 ±5.6 |
| 10.0 | 47.49 ±6.9 | 75.97 ±0.73 | 98.9 ±5 | 87.8 ±4.6 | 78.5 ±6.2 |
| 25.0 | 31.51 ±5.30 | 45.00 ±3.80 | 88.1 ±4.4 | 79.3 ±2.9 | 74.4 ±1.0 |
| 50.0 | 24.54 | 37.34 | 82.5 | 73.2 | 67.0 |

TABLE 5-continued

| [DMBCD] mg/ml | ID-50 mg/ml | ID-80 mg/ml | % 3T3-L1 cell survival exposure time | | |
|---|---|---|---|---|---|
| | | | 1 min | 5 min | 10 min |
| | ±1.14 | ±0.81 | ±6.6 | ±73.2 | ±1.1 |

*n = 3

The formulations were prepared for testing by weighing one gram of the solution and diluting it with Phosphate Buffered Saline (PBS) to 10 ml. A 50 μl aliquot of this dilution was added to a well containing the 3T3-L1 cells. Formulation contents were blinded to analysts. The ID-50 indicates the chemical concentration that reduced the final cellular protein content in the test wells by 50%. The percent survival of cells after a one minute exposure of each formulation show similar results. Hence, it can be concluded that an inclusion compound of DMBCD and thymoxamine, where the formulation contains 5% or less DMBCD, is no more hazardous to a patient than taking thymoxamine alone.

While the invention has been described in terms of a preferred formulation for stabilizing thymoxamine where DMBCD is the essential ingredient that creates an inclusion compound with thymoxamine and thereby prevents hydrolysis, those skilled in the art will recognize that minor variations in the choice of excipients is contemplated within the spirit and scope of the appended claims. Moreover, those skilled in the art will recognize that the concentration of the preferred excipients, including polyvinyl alcohol, dextrose, disodium EDTA, and benzalkonium chloride, can be varied within the scope of the appended claims.

Having thus described our invention, what we intend to secure by Letters Patent is the following:

1. A chemical formulation for preventing hydrolysis of thymoxamine, comprising:
   a therapeutic quantity of thymoxamine hydrochloride; and
   a sufficient quantity of dimethyl-beta-cyclodextrin to form inclusion compounds with said thymoxamine.

2. A chemical formulation as recited in claim 1 wherein said sufficient quantity of dimethyl-beta-cyclodextrin is present in cytologically acceptable amounts.

3. A chemical formulation as recited in claim 1 wherein said sufficient quantity of dimethyl-beta-cyclodextrin and said therapeutic quantity of thymoxamine have a molar ratio of greater than 1.3:1.

4. A chemical formulation as recited in claim 1, wherein said therapeutic quantity of thymoxamine hydrochloride comprises 0.05 to 1.0 weight percent of said chemical formulation, and said sufficient quantity of dimethyl-beta-cyclodextrin comprises 0.5 to 5.0 weight percent of said chemical formulation, said chemical formulation being diluted with a quantity of water to 100 percent by weight.

5. A chemical formulation as recited in claim 4, further comprising the following excipients:
   0.05 to 2.5 weight percent polyvinyl alcohol;
   2.0 to 8.0 weight percent dextrose; and
   0.004 to 0.04 weight percent benzalkonium chloride.

6. A chemical formulation as recited in claim 5 wherein said thymoxamine hydrochloride is present at approximately 0.1 weight percent, said dimethylbeta-cyclodextrin is present at approximately 2.5 weight percent, said polyvinyl alcohol is present at approximately 1.0 weight percent, said dextrose is present at approximately 4.1 weight percent, said disodium edetate is present at approximately 0.03 weight percent, said benzalkonium chloride is present at approximately 0.01 weight percent, and said quantity of water is present at approximately 92.27 weight percent.

7. A chemical formulation as recited in claim 4, further comprising the following excipients:

0.05 to 2.5 weight percent polyvinyl alcohol;

0.0 to 1.0 weight percent sodium chloride; and 0.004 to 0.04 weight percent benzalkonium chloride.

8. A chemical formulation as recited in claim 7 wherein said thymoxamine hydrochloride is present at approximately 0.1 weight percent, said dimethylbeta-cyclodextrin is present at approximately 2.5 weight percent, said polyvinyl alcohol is present at approximately 1.0 weight percent, said sodium chloride is present at approximately 0.08 weight percent, said disodium edetate is present at approximately 0.03 weight percent, said benzalkonium chloride is present at approximately 0.01 weight percent, and said quantity of water is present at approximately 96.28 weight percent.

* * * * *

UNITED STATES PATENT AND TRADEMARK OFFICE
CERTIFICATE OF CORRECTION

PATENT NO. : 5,182,270
DATED : January 26, 1993
INVENTOR(S) : Donald G. Musson; Orest Olejnik, both of Upland, California It is certified that error appears in the above-indentified patent and that said Letters Patent is hereby corrected as shown below:

Column 10 Claim No. 5 should read:

"5. A chemical formulation as recited in claim 4, further comprising the following excipients:

0.05 to 2.5 weight percent polyvinyl alcohol;
2.0 to 8.0 weight percent dextrose;
0.01 to 0.06 weight percent disodium edetate;
and
0.004 to 0.04 weight percent benzalkonium chloride."

Column 11 Claim No. 7 should read:

"7. A chemical formulation as recited in claim 4, further comprising the following excipients:

0.05 to 2.5 weight percent polyvinyl alcohol;
0.0 to 1.0 weight percent sodium chloride;
0.01 to 0.06 weight percent disodium edetate;
and
0.004 to 0.04 weight percent benzalkonium chloride."

Signed and Sealed this

Twenty-sixth Day of April, 1994

Attest:

BRUCE LEHMAN

*Attesting Officer*  *Commissioner of Patents and Trademarks*